United States Patent [19]

Roques et al.

[11] Patent Number: 5,491,169

[45] Date of Patent: Feb. 13, 1996

[54] AMINO ACID DERIVATIVES AND THEIR THERAPEUTICAL APPLICATIONS

[75] Inventors: Bernard Roques, Saint Maurice; Marie C. Fournie-Zaluski, Paris, both of France

[73] Assignee: Institut National de la Sante et de la Recherche Medicale (INSERM), France

[21] Appl. No.: 312,117

[22] Filed: Sep. 26, 1994

Related U.S. Application Data

[63] Continuation of Ser. No. 835,961, filed as PCT/FR90/00627, Aug. 23, 1990, abandoned.

[30] Foreign Application Priority Data

Aug. 24, 1989 [FR] France .................... 89 11224

[51] Int. Cl.⁶ .................................... C07C 321/14
[52] U.S. Cl. .................... 514/529; 514/539; 514/542; 514/550; 560/13; 560/16; 560/125; 560/150; 560/153; 544/159; 546/294
[58] Field of Search .................... 560/13, 16, 125, 560/150, 153; 514/529, 539, 542, 550

[56] References Cited

PUBLICATIONS

Fournie–Zaluski et al., Chemical Abstracts, vol. 117 (1992) No. 70087S.

*Primary Examiner*—Robert W. Ramsuer
*Attorney, Agent, or Firm*—Bierman and Muserlian

[57] ABSTRACT

Compounds having the properties of morphinic substances, particularly analgesia, with beneficial effects on behaviour and with peripheral effects without their major drawbacks (tolerence, addiction), the blood-brain barrier and having the following formula:

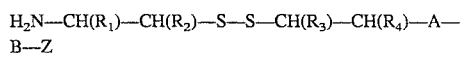

wherein: AB preferably represents a CO amide bond, $R_2$ et $R_3$ preferably represent a hydrogen atom, $R_1$ et $R_4$ preferably represent, independently of each other, a benzyl grouping, $—CH_2CH_2SCH_3$, $—CH_2—CH_2—S(O)—CH_3$ or $—CH_2—CH(CH_3)_2$, Z may represent a $—CH(R_5)[CH(R_6)]_n—COO(R_7)$ grouping wherein: $R_5$ may represent a hydrogen atom, a methyl grouping, a benzyl grouping or a phenyl grouping, $R_6$ may represent a hydrogen atom and may also form a hydrocarbon cycle with $R_5$, or Z may represent a heterocyclic grouping, and preferably a morpholinyl grouping. No drawings.

20 Claims, No Drawings

AMINO ACID DERIVATIVES AND THEIR THERAPEUTICAL APPLICATIONS

PRIOR APPLICATION

This application is a continuation of U.S. patent application Ser. No. 835,961 filed as PCT/FR90/00627, Aug. 23, 1990, now abandoned.

The invention relates to novel amino acid derivatives, to a method for preparing them and to their therapeutical applications.

It is known that natural opioid peptides or enkephalins are essentially degraded by two enzymes belonging to the metallopeptidase class, neutral endopeptidase EC 3.4 24.11 (enkephalinase) which cuts the Gly-Phe$^4$ bond (Malefroy et al., Nature, 27.6, 523, (1978)) and chiefly aminopeptidase N EC 3.4 11.2 which cuts the Tyr$^1$-Gly$^2$ bond (Waksman et al. Eur. J. Pharm., 117, 233 (1985)).

Dipeptide derivatives having activity with respect to enkephalinase (Roques et al.), Nature, 288 286 (1980), French Patent 80/08,601) as well as compounds which inhibit aminopeptidase N (Chan., Biochem. Biophys. Res. Commun. 116 (1983) 297; Chan et al., J. Biol. Chem. 257 (1982) 7955) are known. Similarly, mixed inhibitors of the different enkephalinase activities have been described (Fournié-Zaluski) et al. J. Med. Chem. 28 (1989) 1158; French Patent 86/13,413). Compared to molecules which selectively inhibit neutral endopeptidase or aminopeptidase, these mixed inhibitors display more potent pharmacological properties. However, these compounds which possess a hydroxamate function are very poor at crossing the blood-brain barrier, and hence display considerable analgesic properties only after intracerebroventricular (i.c.v.) injection.

One of the objectives of the invention is to provide novel compounds capable of jointly inhibiting both of the enzymatic activities responsible for the degradation of enkephalins, and of manifesting their pharmacological properties after intravenous (i.v.), subcutaneous (s.c.) or oral (per os) injection.

Another objective of the invention is to provide novel compounds derived from amino acids which display some properties of morphinic substances, especially analgesia, beneficial effects on behavior (sedation, euphoria, reward) and peripheral effects (antidiarrheal, antitussive, hypotensive, anti-inflammatory, etc.) without having their major drawbacks (tolerance, addiction, etc.).

The novel compounds according to the present invention do not possess a hydroxamate function, but are characterized by a disulfide bond.

Moreover, the novel compounds are capable of jointly inhibiting both of the endogenous enkephalin-degrading enzymes or of potentiating the action of exogenously administered analogs.

The subject of the invention is, more especially, compounds corresponding to the formula (I).

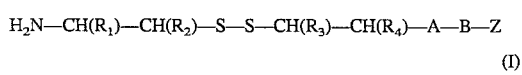
(I)

in which: $R_1$ represents:
- a saturated or unsaturated, linear or branched hydrocarbon chain containing from 1 to 6 carbon atoms, unsubstituted or substituted with a group OR in which R is a hydrogen, a linear or branched C1 to C4 hydrocarbon chain or a phenyl (Phe) or benzyl residue; a thioether group SR, R having the same definition as above, or an oxidized thioether group S(O)R, R having the same definition as above,
- a methylcycloalkyl group containing 5 to 6 carbon atoms, a benzyl or phenyl group, optionally substituted:
  with 1 to 5 halogen, in particular fluorine, atoms,
  or with a group OR' or SR', R' being an alkyl group having 1 to 4 carbon atoms, the thioether SR' being oxidized or otherwise on the sulfur atom,
  or with an amino group optionally mono- or disubstituted with an aliphatic alkyl group having 1 to 6 carbon atoms, oxidized or otherwise on the amine function,
- a methylene group substituted with an aromatic or saturated heterocycle containing 5 or 6 carbon atoms, possessing as the hereto atom a nitrogen atom, an oxygen atom or a sulfur atom, the nitrogen and sulfur atoms optionally being oxidized in the form of N-oxide or S-oxide. $R_2$ independently represents a hydrogen atom or a methyl group. $R_3$ represents a hydrogen atom or a linear or branched alkyl chain. $R_4$ represents:
- a saturated or unsaturated, linear or branched hydrocarbon chain containing from 1 to 6 carbon atoms, unsubstituted or substituted with a hydroxyl group, an ether group OR in which the group R has the same meaning as above, a thiol SH, thioether SR group (R having the same meaning as above) or a thioether group oxidized to sulfoxide,
- a methylcycloalkyl group having 5 to 6 carbon atoms, a benzyl or phenyl group, optionally substituted with 1 to 5 halogen, in particular fluorine, atoms, with a hydroxyl or a thiol, an ether or a thioether OR' or SR', R' having from 1 to 4 carbon atoms, the thioether being oxidized or otherwise on the sulfur atom, with an amino group optionally mono- or disubstituted with an aliphatic alkyl group having 1 to 6 carbon atoms, oxidized or otherwise on the amine function,
- a methylene group substituted with an aromatic or saturated heterocycle containing 5 or 6 carbon atoms, possessing as the hetero atom a nitrogen atom, an oxygen atom or a sulfur atom, the nitrogen and sulfur atoms optionally being oxidized in the form of N-oxide or S-oxide. Z can represent:

* a group —CH($R_5$)—[CH($R_6$)]$_n$—COO($R_7$) in which $R_5$ and $R_6$ can represent, independently of one another:
  a hydrogen,
  a linear or branched alkyl group having 1 to 6 carbon atoms, unsubstituted or substituted with hydroxyl or ether OR, thiol SH or thioether SR groups (R having the definition specified above),
- a phenyl (Phe) or benzyl group unsubstituted or substituted with 1 to 5 halogen atoms; a group OR' or SR', R' having the definition specified above. $R_5$ and $R_6$ can also each represent saturated or unsaturated hydrocarbon chains containing from 1 to 6 carbon atoms in which 1 to 2 carbon atoms may be substituted by an oxygen, sulfur or nitrogen atom, capable of forming one or more saturated or aromatic 5- to 6-membered hydrocarbon rings or saturated or aromatic 5- to 6-membered heterocyclic rings. n can be equal to 0 or 1. $R_7$ represents:
  a hydrogen,
  or a saturated or unsaturated, linear or branched hydrocarbon group having 1 to 6 carbon atoms,
  or a benzyl group.
* a morpholinyl group N—C$_4$—H$_8$O
* piperidyl group —N—C$_5$H$_{10}$ optionally substituted with an —OH residue, a —CO$_2$H residue, a residue COOR$^1$ in which R$^1$ represents a linear or branched alkyl chain containing 1 to 6 carbon atoms, a phenyl residue or a benzyl residue.

* a pyrazolinyl group —N—$C_4H_8$—NH, a substituted pyrazolinyl group —$NC_4H_8$—N—$R^2$ in which $R^2$ represents an alkyl chain containing from 1 to 6 carbon atoms, a benzyl residue or a phenyl residue. A—B represents an amide CONH or retro-amide NHCO group.

The compounds of formula (I) have from 2 to 6 asymmetric carbon atoms. They hence exist in the form of racetalc mixtures and in the forms of enantiomers, of diastereoisomers or of stereoisomers. The subject of the invention is also the addition salts of the compounds of formula (I), obtained with pharmacologically acceptable organic or inorganic acids, such as the hydrochloride, hydrobromide, sulfates, nitrates, borates, phosphates, methanesulfonate, acetate, fumarate, succinate, ascorbate, oxalate, lactate, pyruvate, citrate, tartrate, maleate, malonate, benzoate, salicylate, 2,6-dichlorobenzoate, trimethoxybenzoate, diaminobenzenesulfonate, chromoglycate, benzenesulfonate, cyclohexanesulfonate, toluenesulfonate, dipropylacetate, glucose 1-phosphate, pamoate and palmitate.

Preferably, the compounds according to the invention are such that, in the formula (I), if Z represents a group —$CH(R_5)$—$[CH(R_6)]_n$—COO—$(R_7)$.

$R_2$ and $R_3$ represent hydrogen atoms,

AB represents an amide link CONH, $R_1$ represents a —$CH_2\ CH_2\ S(O)\ CH_3$ group, and $R_7$ represents a —$CH_2$Phe group, in which case they can correspond to the formulae:

$H_2N$—$CH(CH_2CH_2S(O)CH_3)$—$CH_2$—S—S—$CH_2$—$CH(CH_2$PHe$)CONHCH_2COOCH_2$Phe
or
$H_2N$—$CH(CH_2CH_2S(O)CH_3)$—$CH_2$—S—S—$CH_2$—CH—$(CH_2$Phe$)CONH$—$CH(CH_2$Phe$)COOCH_2$Phe
or
$H_2NCH(CH_2CH_2S(O)CH_3)$—$CH_2$—S—S—$CH_2$—$CH(CH_2$PHe$)CONH$—CH—CH—$COOCH_2$Phe

and if $R_4$ represents a —$HC_2CH_2S(O)CH_3$ group, they can correspond to the formulae:

$H_2N$—$CH(CH_2CH_2S(O)CH_3)$—$CH_2S$—S—$CH_2$—$CH(CH_2CH_2S(O)CH_3)$—$CONHCH(CH_3)$—$COOCH_2$Phe
or
$H_2N$—$CH(CH_2CH_2S(O)CH_3)$—$CH_2$—S—S—$CH_2$—$CH(CH_2CH_2S(O)CH_3)CONH$—$CH(CH_2$Phe$)CH_2COOCH_2$Phe
or
$H_2N$—$CH(CH_2CH_2S(O)CH_3)$—$CH_2$—S—S—$CH_2$—$CH(CH_2CH_2S(O)CH_3)CONH$—$CH($Phe$)CH_2COOCH_2$Phe
or
$H_2N$—$CH(CH_2CH_2S(O)CH_3)$—$CH_2$—S—S—$CH_2$—$CH(CH_2CH_2S(O)CH_3)CONH$—CH—CH—$COOCH_2$Phe

The compounds according to the invention can also preferably correspond to the formulae:

$H_2NCH(CH_2CH_2SCH_3)CH_2$—S—S—$CH_2CH(CH_2CH(CH_3)_2)CONHCH(CH_3)COOCH_2$Phe
or
$H_2N$—$CH(CH_2CH_2SCH_3)CH_2$—S—S—$CH_2$—$CH(CH_2$Phe$)CONHCH(CH_3)COOCH_2$Phe
or
$H_2NCH(CH_2CH_2SCH_3)CH_2$—S—S—$CH_2CH(CH_2CH_2SCH_3)CONHCH(CH_3)COOCH_2$Phe
or
$H_2$—$CH(CH_2CH_2SCH_3)CH_2$—S—S—$CH_2$—$CH(CH_2$Phe$)CONHCH(CH_2$Phe$)COOCH_2$Phe
or
$H_2N$—$CH(CH_2CH(CH_3)_2)$—$CH_2$—S—S—$CH_2$—$CH(CH_2$Phe$)CONH$—$CH_2COOCH_2$Phe
or
$H_2N$—$CH(CH_2(CH(CH_3)_2))$—$CH_2$—S—S—$CH_2$—$CH(CH_2$Phe$)CONH$—$CH_2COOCH_2$Phe
or
$H_2N$—$CH(CH_2CH(CH_3)_2)$—$CH_2$—S—S—$CH_2$—$CH(CH_2$Phe$)CONH(CH_2$Phe$)COOCH_2$Phe

-continued or $H_2N-CH(CH_2CH_2SCH_3)-CH_2-S-S-CH_2-CH(CH_2Phe)CONH-CH_2-COOCH_2Phe$ or $H_2N-CH(CH_2CH(CH_3)_2)-CH_2-S-S-CH_2-CH(CH_2Phe)CONH-CH(CH_3)COOCH_2Phe$ or $H_2N-CH(CH_2CH_2S(O)CH_3)CH_2-S-S-CH_2-CH(CH_2CH(CH_3)_2)-CH_2-CONH-N\diagup\hspace{-0.3em}\diagdown O$ 

The latter compounds are especially advantageous on account of their properties of bioavailability (active administered orally).

The subject of the invention is, moreover, a method for preparing the compounds of formula (I) defined above in which Z represents a group $-CH(R_5)-[CH(R_6)]_n-CO(R_7)$ comprising the following steps:

compounds of formula (II):

$R_8NH-CH(R_1)-CH(R_2)SH$ 

in which $R_8$ represents a group protecting group for the amine function, are condensed with dithiodipyridine (III)

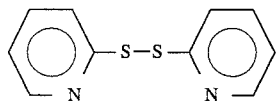

to yield the compounds of general formula (IV):

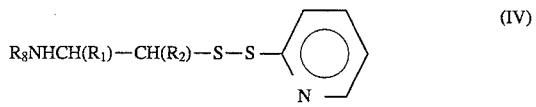 (IV)

the compound (IV) is then condensed with the compounds of formula (V):

$HS-CH(R_3)-CH(R_4)-A-B-CH(R_5)-[CH(R_6)]_n-COO(R_7)$ 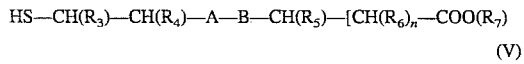

(V)

to yield the compounds of the formula (VI):

$R_8NH-CH(R_1)-CH(R_2)-S-S-CH(R_3)-CH(R_4)-A-B-CH(R_5)-[CH(R_6)]_n-COO(R_7)$ 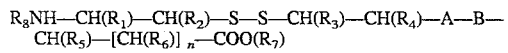

the amine function of the compound (VI) is then deprotected to yield the compound of formula (I).

Preferably, the condensation of the compound of formula (II) with dithiopyridine (III) is performed at room temperature in the presence of acetic acid in ethanol.

The condensation of the intermediate compound (IV) with the compound (V) is performed in ethanol at room temperature.

The intermediate products (II) and (V) are synthesized according to the procedures described in the literature (Chan, Biochem. Biophys. Res. Commun., 116, 297, (1983) and Cushman et al., Biochemistry, 16, 5484, (1977)).

The protective group $R_8$ is preferably t-butyloxy carbonyl (t. Boc). This group may be removed using trifluoroacetic acid in methylene chloride.

If $R_2$ represents a hydrogen atom, the product of formula (II) may be obtained from a beta-amino alcohol of formula:

$H_2N-CH-(R_1)-CH_2OH$ (VII) 

- by protection of the amine function using a group $R_8$, resulting in the formation of the product of formula:

$R_8NH-CH(R_1)-CH_2OH$ (VIII) 

then by activation of the alcohol function, in particular in the form of rosylate, resulting in the formation of a product of formula:

$R_8NH-CH(R_1)\ CH_2OT_S$ (IX) 

in which $T_S$ represents a rosylate group,

- then by conversion of the tosylate group to an acetylthio group, resulting in the formation of the product of formula:

$R_8NH-CH(R_1)-CH_2-S-COCH_3$ (X) 

- then by alkaline hydrolysis of the product (X) in a reducing atmosphere, resulting in the formation of the compound of formula (II).

The beta-amino alcohol products of formula (VII) are obtained by a protocol described in the literature [(Chan. Biochem. Biophys. Res. Commun. 116 297 (1983)].

If $R_2$ represents a hydrogen atom, the product of formula (X) may be obtained from the product of formula (VIII) under the conditions of the Mitsunobu reaction (Synthesis (1981), 1–28), that is to say in the presence of triphenylphosphine and a dialkyl azodicarboxylate.

If $R_2$ represents a $-CH_3$ group and if $R_1$ and $R_4$ have the same meaning, the compound of formula (II) may be prepared by a Curtius rearrangement (Pataï, The Chemistry of Azides groups, 397, (1971)) from a compound of formula:

$CH_3-CO-SCH(CH_3)CHR_1-CO_2H$ (XI) 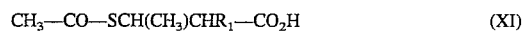

by treatment of said compound with sodium azide $NaN_3$ in the presence of dicyclohexylcarbodiimide (DCC), resulting in the formation of the product of formula:

$CH_3-CO-SCH(CH_3)CHR_1-CON_3$ (XII) 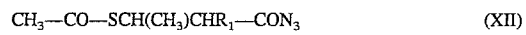

then by heating in the presence of an alcohol, resulting in the formation of the product of formula:

$CH_3-CO-SCH(CH_3)CHR_1-NHR_8$ (XIII) 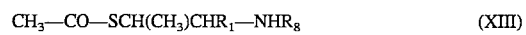

then by acid hydrolysis of the acetylthio group under reducing conditions.

Preferably, the amine function of the compound (XIII) is protected in the form of carbamate.

If $R_3$ represents a hydrogen atom or a $-CH_3$ group, and AB an amide group CONH, the compound of formula (V) may be obtained from a compound of formula:

$CH_3-CO\ S\ CH(R_3)CH(R_4)-CO_2H$ (XIV) 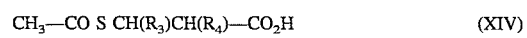

which are 2-substituted (acetylthio)propanoic (sic) acids (Cushman et al. (1977), Biochemistry 16 5484).

- by alkaline hydrolysis of said compound, preferably under oxidizing conditions, resulting in the formation of the compound of formula:

$(SCH(R_3)CH(R_4)-CO_2H)_2$ (XV) 

followed by condensation under conventional conditions of peptide coupling with an amino ester of formula:

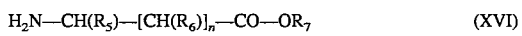

$$H_2N—CH(R_5)—[CH(R_6)]_n—CO—OR_7 \qquad (XVI)$$

resulting in the formation of a compound of formula:

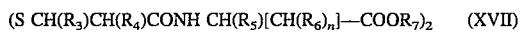

$$(S\ CH(R_3)CH(R_4)CONH\ CH(R_5)[CH(R_6)_n]—COOR_7)_2 \qquad (XVII)$$

followed by treatment in a reducing medium (zinc and hydrochloric acid).

The beta-amino acids of formula (XVI) are synthesized by conventional methods (Xie et al., J. Med. Chem. (1989), 32, 1497).

The compound of formula XI may be obtained from the phosphorus ylide of formula:

$$(Phe)_3P—CH(R_1)—COO—CH_3 \qquad (XVIII)$$

by Witting condensation with acetaldehyde, resulting in the formation of the compound of formula:

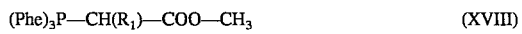

$$CH_3CH=C(R_1)—CO—)CH_3 \qquad (XIX)$$

then by alkaline hydrolysis, resulting in the formation of the compound of formula:

$$CH_3CH=C(R_1)CO_2H \qquad (XX)$$

then by addition of thioacetic acid.

If $R_3$ represents a hydrogen atom or a —$CH_3$ group and if $R_1$ and $R_4$ have the same meaning and if AB represents a retro-amide group NHCO, the compound of formula (V) may be prepared, respectively, from the compounds (X) and (XIII) corresponding to the general formula:

$$CH_3CO—S—CH(R_2)CH(R_1)NHR_8 \qquad (XXI)$$

by alkaline hydrolysis under oxidizing conditions, resulting in the formation of the compound of formula:

$$[SCH(R_2)CH(R_1)NMR_8]_2 \qquad (XXII)$$

then by deprotection of the amine function, yielding the compound of formula:

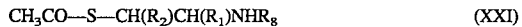

$$[SCH(R_2)CH(R_1)NH_2]_2 \qquad (XXIII)$$

then by condensation under conventional conditions of peptide coupling with malonic or succinic acid monoesters of formula:

$$CO_2H—CH(R_5)—[CH(R_6)]_n—COOR_7 \qquad (XXIV)$$

resulting in the formation of a compound of formula:

$$[SCH(R_2)CHR_1—NHCO—CHR_5—(CHR_6)_n—COOR_7]_2$$

then by treatment in a reducing medium.

The malonic or succinic acid monoesters of formula (XXIV) are synthesized by conventional methods (Fournie-Zaluski et al., Int. J. Pept. Prot. Res., 33, (1989), 146).

The subject of the invention is, in addition, a method for preparing the compounds of formula I in which the group Z represents:
* a morpholinyl group N—$C_4H_8O$
* a piperidyl group —N—$C_5H_{10}$ optionally substituted with an —OH residue, a —$CO_2H$ residue, a residue $COOR^1$ in which $R^1$ represents a linear or branched alkyl chain containing 1 to 6 carbon atoms, a phenyl residue or a benzyl residue.
* a pyrazolinyl group —N—$C_4H_8$—NH, a substituted pyrazolinyl group —$NC_4H_8$—N—$R^2$ in which $R^2$ represents an alkyl chain containing from 1 to 6 carbon atoms, a benzyl residue or a phenyl residue characterized in that compounds of formula

$$(SCH(R_3)CH(R_4)—CO_2H)_2 \qquad (XV)$$

are condensed with a hydrazine of formula

$$H_2N—Z \qquad (XXV)$$

resulting in the formation of a compound of formula

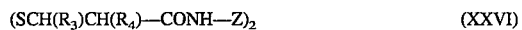

$$(SCH(R_3)CH(R_4)—CONH—Z)_2 \qquad (XXVI)$$

which is condensed with a compound of formula

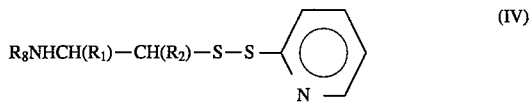

to yield the compound of formula (I).

Another subject of the invention is a pharmaceutical composition containing at least one compound as defined above, or obtained by the method as defined above, in combination with one or more compatible or pharmaceutically acceptable diluents or adjuvants.

These compositions may be used, in particular, as a major analgesic, as an antalgic and as an anti-depressant. These compounds are almost devoid of the side effects of morphinics (tolerance and addiction). Their main application is hence in the field of analgesia and antidepressants.

Another subject of the invention is the application of the compounds as defined above, or obtained by a method as defined above, as medicinal products.

The invention will be further illustrated, without being in any way limited, by the examples below:

The list of compounds prepared according to Examples 1 to 32 is given in Table I.

For all the compounds described in this table, $R_2$ and $R_3$ both represent hydrogen atoms, $R_7$ represents a —$CH_2Phe$ group and AB an amide link CONH.

TABLE I

| Example | $R_1$ | $R_4$ | $R_5$ | $R_6$ |
|---|---|---|---|---|
| 1 | $CH_2CH(CH_3)_2$ | $CH_2Phe$ | H | — |
| 2 | $CH_2CH(CH_3)_2$ | $CH_2Phe$ | $CH_3$ | — |
| 3 | $CH_2CH(CH_3)_2$ | $CH_2Phe$ | $CH_2Phe$ | — |
| 4 | $CH_2Phe$ | $CH_2Phe$ | H | — |
| 5 | $CH_2CH_2SCH_3$ | $CH_2Phe$ | H | — |
| 6 | $CH_2CH_2SCH_3$ | $CH_2Phe$ | $CH_3$ | — |
| 7 | $CH_2CH_2SCH_3$ | $CH_2Phe$ | $CH_2Phe$ | — |
| 8 | $CH_2CH_2S(O)CH_3$ | $CH_2Phe$ | H | — |
| 9 | $CH_2SCH_3$ | $CH_2Phe$ | H | — |

TABLE I-continued

| Example | R$_1$ | R$_4$ | R$_5$ | R$_6$ |
|---|---|---|---|---|
| 10 | CH$_2$S(O)CH$_3$ | CH$_2$Phe | H | — |
| 11 | CH$_2$SCH$_2$Phe | CH$_2$Phe | H | — |
| 12 | CH$_2$S(O)CH$_2$Phe | CH$_2$Phe | H | — |
| 13 | CH$_2$CH$_2$SCH$_3$ | CH$_2$CH(CH$_3$)$_2$ | CH$_3$ | — |
| 14 | CH$_2$CH$_2$S(O)CH$_3$ | CH$_2$CH(CH$_3$)$_2$ | CH$_3$ | — |
| 15 | CH$_2$SCH$_3$ | CH$_2$CH(CH$_3$)$_2$ | CH$_3$ | — |
| 16 | CH$_2$S(O)CH$_3$ | CH$_2$CH(CH$_3$)$_2$ | CH$_3$ | — |
| 17 | CH$_2$SCH$_2$Phe | CH$_2$CH(CH$_3$)$_2$ | CH$_3$ | — |
| 18 | CH$_2$S(O)CH$_2$Phe | CH$_2$CH(CH$_3$)$_2$ | CH$_3$ | — |
| 19 | CH$_2$St Bu | CH$_2$CH(CH$_3$)$_2$ | CH$_3$ | — |
| 20 | CH$_2$S(O)tBu | CH$_2$CH(CH$_3$)$_2$ | CH$_3$ | — |
| 21 | CH$_2$CH$_2$SCH$_3$ | CH$_2$CH$_2$SCH$_3$ | CH$_3$ | — |
| 22 | CH$_2$CH$_2$S(O)CH$_3$ | CH$_2$CH$_2$S(O)CH$_3$ | CH$_3$ | — |
| 23 | CH$_2$CH$_2$SCH$_3$ | CH$_2$Phe | Phe | H |
| 24 | CH$_2$CH$_2$S(O)CH$_3$ | CH$_2$Phe | Phe | H |
| 25 | CH$_2$CH$_2$SCH$_3$ | CH$_2$Phe | CH$_2$—CH$_2$—CH$_2$—CH$_2$ | |
| 26 | CH$_2$CH$_2$S(O)CH$_3$ | CH$_2$Phe | CH$_2$—CH$_2$—CH$_2$—CH$_2$ | |
| 27 | CH$_2$CH$_2$SCH$_3$ | CH$_2$CH$_2$SCH$_3$ | Phe | H |
| 28 | CH$_2$CH$_2$S(O)CH$_3$ | CH$_2$CH$_2$S(O)CH$_3$ | Phe | H |
| 29 | CH$_2$CH$_2$SCH$_3$ | CH$_2$CH$_2$SCH$_3$ | CH$_2$Phe | H |
| 30 | CH$_2$CH$_2$S(O)CH$_3$ | CH$_2$CH$_2$S(O)CH$_3$ | CH$_2$Phe | H |
| 31 | CH$_2$CH$_2$SCH$_3$ | CH$_2$CH$_2$SCH$_3$ | CH$_2$—CH$_2$—CH$_2$—CH$_2$ | |
| 32 | CH$_2$CH$_2$S(O)CH$_3$ | CH$_2$CH$_2$S(O)CH$_3$ | CH$_2$—CH$_2$—CH$_2$—CH$_2$ | |

EXAMPLE 1

Preparation of
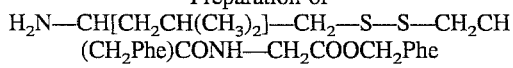

Step 1 Preparation of

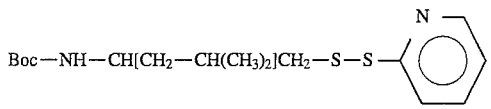

A solution of 1.6 g of Boc—NH—CH[CH$_2$—CH(CH$_3$)$_2$]—CH$_2$—SH in 5 ml of outgassed ethanol is added to a solution of 3 g of 2,2'-dithiodipyridine in 5 ml of out-gassed ethanol and 0.35 ml of acetic acid, and the mixture is stirred for 24 h at room temperature. It is evaporated to dryness. A yellow oil is obtained, which is chromatographed on silica gel in a 9:1.25:0.25 cyclohexane/ethyl acetate/acetic acid mixture. 1.62 g of the expected product are obtained. Yld 72%; Rf (8:2 cyclohexane/ethyl acetate)=0.25

Step 2 Preparation of Boc—NH—CH—[CH$_2$CH(CH$_3$)$_2$]CH$_2$—S—S—CH$_2$CH (CH$_2$Phe)—CONH—CH$_2$—COO—CH$_2$Phe A solution of 1.7 g of N-(2-mercaptomethyl-3-phenyl-1-oxopropylglycine benzyl ester in 10 ml of outgassed ethanol is added to a solution of 1.6 g of the above compound in 10 ml of outgassed ethanol. The mixture is stirred for 24 h at room temperature. It is evaporated to dryness. A yellow oil is obtained, chromatographed on silica gel with a 7:3:0.5 cyclohexane/EtOAc/AcOH mixture as eluent.

2.42 g (Yld 86%) of the expected product are obtained. Rf (8:2:0.5 cyclohexane/ethyl acetate/acetic acid)=0.38.

Step 3 Preparation of the final product 2.4 g of the above compound are dissolved in 4 ml of CH$_2$Cl$_2$·6 ml of trifluoroacetic acid (TFA) are added at 0° C. The mixture is stirred for 2 h at 0° C. and 2 h at room temperature. It is evaporated to dryness. It is chromatographed on silica gel using a 20:1 CH$_2$Cl$_2$/MeOH mixture as eluent. 1.63 g of the expected product are obtained (Yld 80%). Rf (9:1 CH$_2$Cl$_2$/MeOH)= 0.46.

EXAMPLE 2

Preparation of
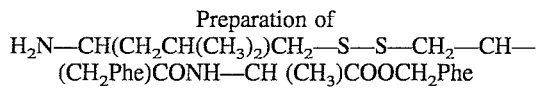

Starting with 0.685 g of 2-boc-amino-4-methyl- 1-pentyl-1'-dithiopyridine prepared in Example 1, step 1, and 0.715 g of N-[2-mercaptomethyl-3-phenyl- 1-oxopropyl]alanine benzyl ester, and according to the conditions of Example 1, step 2, the protected inhibitor (0.88 g, 75%) is obtained. After deprotection, the expected compound (0.57 g, 80%) is obtained in the form of an oily product, Rf (8:2:0.5 cyclohexane/EtoAC/AcOH)=0.39. Mass spectrum CI, NH$_3$ (M+1)=489.

EXAMPLE 3

Preparation of
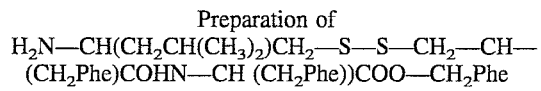

Starting with 0.685 g of 2-boc-amino-4-methyl- 1-pentyl-1'-dithiopyridine prepared in Example 1, step 1, and 0.870 g of N-[2-mercaptomethyl-3-phenyl- 1-oxopropyl]phenylalanine benzyl ester, and according to the conditions of Example 1, step 2, the protected inhibitor (0.90 g, 60%) is obtained. After deprotection, the expected compound (0.554 g, 72%) is obtained, Rf (8:2:0.5 cyclohexane/EtoAC/AcOH)=0.41. Mass spectrum CI, NH$_3$ (M+1)=565.

EXAMPLE 4

Preparation of
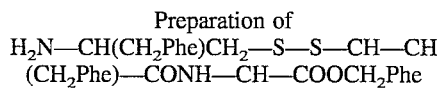

Step 1 Preparation of

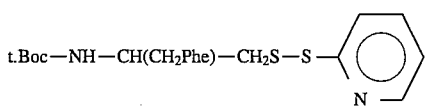

Starting with 410 mg of 2,2'-dipyridyl disulfide and 250 mg of 2-t-Boc-amino-3-phenyl-1-propanethiol, and following the working conditions of Example 1, 170 mg (Yld 42%) of the expected product are obtained in the form of an oil. Rf (9:10:0.5 cyclohexane/EtoAC/AcOH)=0.26.

Step 2 Preparation of t-Boc-NH-CH(CH$_2$Phe)—CH$_2$S—S—CH$_2$CH—(CH$_2$Phe)—CONH—COO—CH$_2$Phe Starting with 170 mg of the above compound and 160 mg of N-(2-mercaptomethyl-3-phenyl-1-oxopropyl)-glycine benzyl ester, and following the experimental conditions of Example 1, 174 mg (61%) of the expected product are obtained in the form of an oil: Rf (7:3:0.5 cyclohexane/EtoAC/AcOH)=0.54.

Step 3 Preparation of the final product

Starting with 170 mg of the above compound, and following the experimental conditions of Example 1, 80 mg (Yld 55%) of the expected product are obtained in oily form. Rf (9:1CH$_2$Cl$_2$/MeOH)=0.56.

EXAMPLE 5

Preparation of
H$_2$N—CH(CH$_2$CH$_2$SCH$_3$)—CH$_2$—S—S—CH$_2$—CH(CH$_2$Phe)—CONH—CH$_2$Phe Step 1 Preparation of

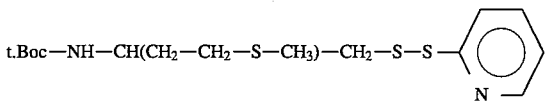

Starting with 0.82 g of 2-t-Boc-amino-4-mercaptomethyl-1-butanethiol and 1.43 g of 2,2'-dipyridyl disulfide, and following the procedure of Example 1, 0.77 g (Yld 68%) of the expected product is obtained in the form of an oil. Rf (8:2:0.5 cyclohexane/Et/AOc/AcOH)=0.32.

Step 2 Preparation of t-Boc—NH—CH(CH$_2$—CH$_2$—S—CH$_3$)-CH$_2$—S—S—CH$_2$CH (CH$_2$Phe)CONH—CH$_2$—COO—CH$_2$Phe Starting with 0.75 g of the above compound and 0.76 g of N-(2-mercaptomethyl-3-phenyl-1-oxopropyl)-glycine benzyl ester, and following the experimental conditions of Example 1, 1.18 g (Yld 87%) of the expected product are obtained in the form of an oil. Rf (cyclohexane/EtoAc/AcOH (8.2:0.5)=0.46.

Step 3 Preparation of the final product

Starting with 0.4 g of the above compound, and using the experimental conditions of Example 1, 0.35 g of the expected product (Yld 85%) is obtained in the form of, an oil. Rf (9:1CH$_2$Cl$_2$/MeOH)=0.50.

EXAMPLE 6

Preparation of
H$_2$N—CH(CH$_2$CH$_2$SCH$_3$)CH$_2$—S—S—CH$_2$—CH (CH$_2$Phe)CONH—CH (CH$_3$)COOCH$_2$Phe Starting with 0.9 g of 2-boc-amino-4-mercaptomethyl-1-butyl-1'-dithiopyridine prepared in Example 1, step 1, and 0.88 g of N-[2-mercaptomethyl-4-phenyl-1-oxopropyl]alanine benzyl ester, and according to the conditions of Example 1, step 2, the protected inhibitor (1.07 g, Yld 70%) is obtained. After deprotection according to the method of Example 1, step 3, 0.66 g (75%) of the expected product is obtained. Rf (9:1:0.5 CH$_3$/MeOH/AcOH)=0.62. Mass. Spectrum CI, NH$_3$(MH)=501.

EXAMPLE 7

Preparation of
H$_2$N—CH(CH$_2$CH$_2$SCH$_3$)CH$_2$—S—S—CH$_2$—CH—(CH$_2$Phe)
—CONH—CH$_2$—CH$_2$—Phe)—COOCH$_2$Phe.

Starting with 0.7 g of 2-boc-amino-4-mercaptomethyl-1-butyl-1'-dithiopyridine prepared in Example 1, step 1, and 0.9 g of N-[2-mercaptomethyl-3-phenyl- 1-oxopropyl]phenylalanine benzyl ester, and according to the conditions of Example 1, step 2, the protected inhibitor (08 g, Yld 60%) is obtained. After deprotection according to the method of Example 1, step 3, 0.616 g (72%) of the expected product is obtained. Rf (9:1:0.5 CHCl$_3$/MeOH/AcOH)=0.65 and 0.75. Mass spectrum CI, NH$_3$ (M+1)=583.

EXAMPLE 8

Preparation of
H$_2$N-CH(CH$_2$CH$_2$S(O)CH$_3$)—CH$_2$S—S—CH$_2$—CH (CH$_2$Phe) CONH—CH$_2$COOCH$_2$Phe This compound is obtained from the compound of Example 5, protected on the amine function (step 2). Oxidation of 0.5 g of this compound with sodium periodate (1 eq) in an aqueous-alcoholic medium enables 0.380 g of the corresponding sulfoxide, which is an oily product, to be obtained. Rf (7:3:0.5 cyclohexane/EtoAC/AcOH)= 0.20 (Yld 78%).

Treatment with trifluoroacetic acid in the same manner as in step 3 of Example 1 enables the expected final compound to be liberated. M=0.289 g (Yld 85%) Rf (9:1CH$_2$Cl$_2$/MeOH)=0.25.

EXAMPLE 9

Preparation of H$_b$,
2N—CH(CH$_2$SCH$_3$)CH$_2$—S—S—CH$_2$—CH(CH$_2$Phe)
—CONHCH$_2$—COOCH$_2$Phe Step 1 Preparation of

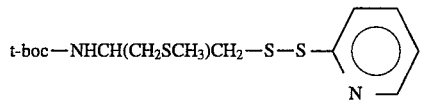

Starting with 2.2 g of 2-(N-t-Boc-amino)-1-mercapto-3-(methylthio)propane, and under the conditions of Example 1, step 1, 2.3 g of the expected product (70%) are obtained, RE (8:2 cyclohexane) EtOAc)=0.28.

Step 2 Preparation of t-Boc NHCH (CH$_2$SCH$_3$)CH$_2$—S—S—CH$_2$—CH(CH$_2$Phe) CONHCH$_2$COOCH$_2$Phe Starting with 2.2 g of the above compound, and under the conditions of Example 1, step 2, 3.07 g (82%) of the expected product are obtained. Rf (7:3:0.5 cyclohexane/EtOAc/AcOH)=0.52.

Step 3 Preparation of the final product

Starting with 3 g of the above compound, and under the conditions of Example 1, step 3, 1.99 g of the expected compound (Yld 78%) are obtained - Rf (9:1 CH$_2$Cl$_2$/MeOH) - 0.38.

EXAMPLE 10

Preparation of
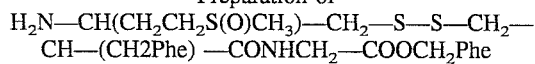
H$_2$N—CH(CH$_2$CH$_2$S(O)CH$_3$)—CH$_2$—S—S—CH$_2$—CH—(CH2Phe)—CONHCH$_2$—COOCH$_2$Phe This compound is obtained from the final compound of Example 9, protected on the amine function, (step 2). Oxidation under the conditions of Example 9 yields the corresponding sulfoxide (Yld 45%) Rf (7:3:0.5 cyclohexane/EtoAC/AcOH)=0.30.

Treatment with TFA (conditions of Example 1, step 3) liberates the expected compound. Rf (7:3 CH$_2$Cl$_2$/MeOH)= 0.35 (Yld 80%).

EXAMPLE 11

Preparation of
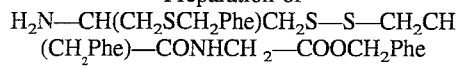
H$_2$N—CH(CH$_2$SCH$_2$Phe)CH$_2$S—S—CH$_2$CH(CH$_2$Phe)—CONHCH$_2$—COOCH$_2$Phe Step 1 Preparation of

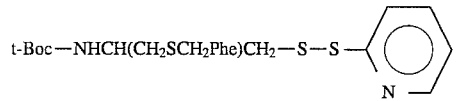

Starting with 1.48 g of 2-(N-t-Boc-amino)-1-mercapto-3-(benzylthio)propane, and under the conditions of Example 1, step 1, 1.3 g (Yld 68%) of the expected product are obtained. Rf (7:3 cyclohexane/EtOAc)=0.31.

Step 2 Preparation of t-Boc NH—CH(CH$_2$SCH$_2$Phe)CH$_2$—S—S—CH$_2$—CH(CH$_2$Phe)CONH—CH$_2$COO—CH$_2$Phe Starting with 1.38 g of the above compound, and under the conditions of Example 1, step 2, 1.73 g (Yld 80%) of the expected compound are obtained. Rf (7:3:0.5 cyclohexane/EtOAc/AcOH)=0.55.

Step 3 Preparation of the final compound

Starting with 1.7 g of the above compound, and under the conditions of Example 1, step 3, 1.04 g (70%) of the expected product are obtained. Yld (8:2 CH$_2$Cl$_2$/MeOH)= 0.43.

EXAMPLE 12

Preparation of
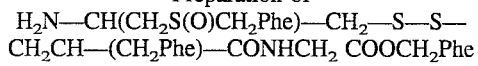
H$_2$N—CH(CH$_2$S(O)CH$_2$Phe)—CH$_2$—S—S—CH$_2$CH—(CH$_2$Phe)—CONHCH$_2$ COOCH$_2$Phe This compound is obtained from the compound of Example 11, protected on the amine function (step 2). Oxidation under the conditions of Example 8 leads to the corresponding sulfoxide Yld (70%) Rf (7:3:0.5 cyclohexane/EtoAc/AcOH)=0.32

Treatment with TFA (Example 1, step 3) liberates the expected compound Rf (7:3 CH$_2$Cl$_2$/MeOH)= 0.48 (Yld 82%).

EXAMPLE 13

Preparation of
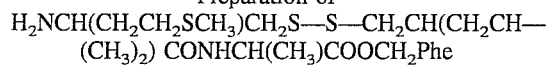
H$_2$NCH(CH$_2$CH$_2$SCH$_3$)CH$_2$S—S—CH$_2$CH(CH$_2$CH—(CH$_3$)$_2$) CONHCH(CH$_3$)COOCH$_2$Phe 1.7 g of the compound obtained in Example 5, step 1, is condensed under the conditions of Example 1, step 2, with 1.6 g of benzyl N-(2-mercaptomethyl-4-methyl-1-oxopentyl)alaninate. 1.94 g (Yld 70%) of the final compound, protected on the amine function, are obtained. Rf (7:3:0.5 cyclohexane/EtOAc/AcOH)=0.41.

Treatment with TFA (Example 1, step 3) liberates the expected final compound (1.35 g) (Yld 83%) Rf (8:2 CH$_2$Cl$_2$/MeOH) 0.51.

EXAMPLE 14

Preparation of
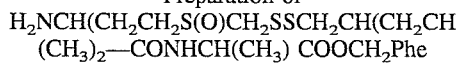
H$_2$NCH(CH$_2$CH$_2$S(O)CH$_2$SSCH$_2$CH(CH$_2$CH(CH$_3$)$_2$—CONHCH(CH$_3$) COOCH$_2$Phe The compound of Example 13, protected on the amine function, is oxidized under the conditions described for Example 8. After deprotection with TFA (Example 1, step 3), the expected inhibitor is obtained. Overall Yld 60%. Rf (8:2 CH$_2$Cl$_2$/MeOH)=0.36.

EXAMPLE 15

Preparation of
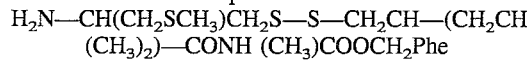
H$_2$N—CH(CH$_2$SCH$_3$)CH$_2$S—S—CH$_2$CH—(CH$_2$CH(CH$_3$)$_2$)—CONH (CH$_3$)COOCH$_2$Phe 1.65 g of the compound (Example 9, step 1) is condensed under the conditions of Example 1, step 2, with 1.6 g of benzyl N-(2-mercaptomethyl-4-methyl-1-oxopentyl)alaninate. 1.89 g (Yld 70%) of the compound protected on the amine function are obtained. Rf (7:3:0.5 cyclohexane/EtOAc/AcOH)=0.45.

Treatment with TFA (Example 3, step 1) liberates the final compound (1.32 g) (Yld 82%) Rf (8:2 CH$_2$Cl$_2$/MeOH)= 0.60.

EXAMPLE 16

Preparation of
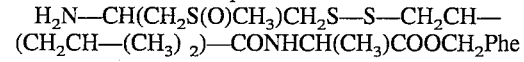
H$_2$N—CH(CH$_2$S(O)CH$_3$)CH$_2$S—S—CH$_2$CH—(CH$_2$CH—(CH$_3$)$_2$)—CONHCH(CH$_3$)COOCH$_2$Phe The compound of Example 15, protected on the amine function, is oxidized under the conditions described for Example 8. After deprotection with TFA (Example 1, step 3), the expected final compound is obtained. Overall Yld 55%. Rf (8:2 CH$_2$Cl$_2$/MeOH)=0.38

EXAMPLE 17

Preparation of
H$_2$NCH(CH$_2$SCH$_2$Phe]CH$_2$S—S—CH$_2$CH—(CH$_2$CH—(CH$_3$)$_2$)—CONHCH (CH$_3$)COOCH$_2$Phe The compound (Example 11, step 1) (1 g) is condensed under the conditions of Example 1, step 2, with 1.07 g of benzyl N-(2-mercaptomethyl-4-methyl-1-oxopentyl)alaninate. 1.34 g (Yld 65%) of the final compound protected on the amine function are obtained. Rf (7:3:0.5 cyclohexane/EtOAc/AcOH)=0.42. Treatment with TFA (Example 1, step 3) liberates the final compound (0.99 g) (Yld 86%) Rf (8:2

EXAMPLE 18

Preparation of
H$_2$N—CH(CH$_2$S(O)CH$_2$Phe)CH$_2$S—S—CH$_2$CH—(CH$_2$CH(CH$_3$)$_2$)—CONHCH(CH$_3$)COOCH$_2$Phe The final compound of Example 17, protected on the amine function, is oxidized under the conditions described for Example 8. After deprotection with TFA (Example 1, step 3), the expected final compound is obtained. Overall Yld (73%) Rf (7:3 CH$_2$Cl$_2$/MeOH)= 0.52.

EXAMPLE 19

Preparation of
H$_2$N—CH(CH$_2$StBu)CH$_2$S—S—CH$_2$CH—(CH$_2$CH(CH$_3$)$_2$)—CONHCH(CH$_3$)COOCH$_2$Phe Starting with 0.93 g of t-Boc-S-t-butylcysteinethiol, and under the conditions of Example 1, step 1, 1.06 g (Yld 80%) of the corresponding disulfide are obtained. This compound is then condensed under the conditions off Example 1, step 2, with 0.86 g of benzyl N-(2-mercaptomethyl-4-methyl-1-oxopentyl)alaninate. 1.19 g of the protected final compound (Yld 75%) are obtained. Rf (7:3:0.5 cyclohexane/EtOAc/AcOH)=0.31. Treatment with TFA liberates the final compound (0.84 g) (Yld 85%) Rf (7:3 CH$_2$Cl$_2$/MeOH)=0.38.

EXAMPLE 20

Preparation of
H$_2$N—CH(CH$_2$S(O)tBu)CH$_2$S—S—CH$_2$CH—(CH$_2$CH(CH$_3$)$_2$)CONHCH(CH$_3$) COOCH$_2$Phe The compound of Example 19, protected on the amine function, is oxidized under the conditions described for Example 8. After deprotection with TFA (Example 1, step 3), the expected final compound is obtained. (Overall Yld 68%) Rf (7:3 CH$_2$Cl$_2$/MeOH)= 0.30.

EXAMPLE 21

Preparation of
H$_2$NCH(CH$_2$CH$_2$SCH$_3$)CH$_2$—S—S—CH$_2$—CH—(CH$_2$CH$_2$SCH$_3$)—CONHCH(CH$_3$)COOCH$_2$Phe 1.71 g of the disulfide (Example 5, step 1) is condensed under the conditions of Example 1, step 2, with 1.70 g of benzyl N-(2-mercaptomethyl-4-methylmercapto-1-oxobutyl)alaninate. 2.1 g (72%) of the final compound protected on the amine function are obtained. Rf (7:3:0.5 cyclohexane/EtOAc/AcOH) 0.58. Treatment with TFA (Example 1, step 3) liberates the final compound (1.18 g) (Yld 68%) Rf (7:3 CH$_2$Cl$_2$/MeOH): 0.42.

EXAMPLE 22

Preparation of
H$_2$N—CH(CH$_2$CH$_2$S(O)CH$_3$)CH$_2$—S—S—CH$_2$—(CH$_2$CH$_2$S(O) CH$_3$)CONHCH(CH$_3$)COOCH$_2$Phe The final compound of Example 21, protected on the amine function, is oxidized under the conditions described for Example 8. After deprotection with TFA (Example 1, step 3), the expected final compound is obtained. Overall Yld 56%.

EXAMPLE 23

Preparation of
H$_2$NCH(CH$_2$CH$_2$SCH$_3$)CH$_2$—S—S—CH$_2$—CH—(CH$_2$Phe) CONH—CH(Phe)CH$_3$COOCH$_2$Phe 1.19 g of the disulfide (Example 5, step 1) is condensed under the conditions of Example 1, step 2, with 1.44 g of benzyl N-(2-mercaptomethyl-3-phenyl-1-oxopropyl)3-phenyl-beta-alaninate. 1.59 g (Yld 70%) of the final compound protected on the amine function are obtained. Rf (7:3:0.5 cyclohexane/EtOAc/AcOH): 0.28. Treatment with TFA (Example 1, step 3) liberates the final compound (1.15 g) (Yld 85%) Rf (7:3 CH$_2$Cl$_2$/MeOH)= 0.60.

EXAMPLE 24

Preparation of
H$_2$NCH(CH$_2$CH$_2$S(O)CH$_3$)CH$_2$—S—S—CH$_2$CH—(CH$_2$Phe)CONHCH(Phe)CH$_2$ COOCH$_2$Phe The final compound of Example 23, protected on the amine function, is oxidized under the conditions described for Example 8. After deprotection with TFA (Example 1, step 3), the expected final compound is obtained. (Overall Yld 58%). Rf (7:3 CH$_2$Cl$_2$/MeOH)= 0.25.

EXAMPLE 25

Preparation of

0.895 g of the disulfide (Example 5, step 1) is condensed under the conditions of Example 1, step 2, with 1.027 g of benzyl 2-[N-(2-mercaptomethyl-3-phenyl-1-oxopropyl)amino]-cyclohexanecarboxylate. 1.12 g (Yld 68%) of the final product protected on the amine function are obtained. Rf (7:3:0.5 cyclohexane/EtOAc/AcOH)=0.32. Treatment with TFA (Example 1, step 3) liberates the final compound (0.78 g) (Yld 82%) Rf (7:3 CH$_2$Cl$_2$/MeOH): 0.63.

EXAMPLE 26

Preparation of

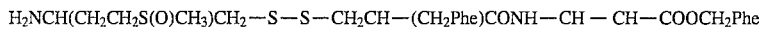

The final compound of Example 25, protected on the amine function, is oxidized under the conditions described in Example 8. After deprotection with TFA, (Example 1, step 3), the expected compound is obtained. Overall Yld 62%. Rf (8:2 $CH_2Cl_2$/MeOH)=0.28.

EXAMPLE 27

Preparation of
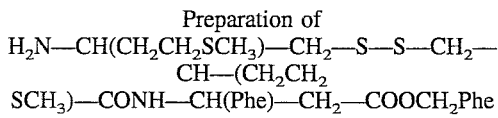

1.1 g of the disulfide (Example 5, step 1) are condensed under the conditions of Example 1, step 2, with 1.39 g of benzyl 3-[N-(2-mercaptomethyl-4-methylmercapto-1-oxobutyl)amino]-phenyl-propanoate. 1.44 g (Yld 65%) of the final compound protected on the amine function are obtained. Rf (7:3:0.5 cyclohexane/EtOAc/AcOH)=0.42. Treatment with TFA (Example 1, step 3) liberates the final compound (1.01 g) (Yld 85%) Rf (7:3 $CH_2Cl_2$/MeOH): 0.72.

EXAMPLE 28

Preparation of
$H_2N\text{---}CH(CH_2CH_2S(O)CH_3)CH_2\text{---}S\text{---}S\text{---}CH_2\text{---}CH(CH_2\text{---}CH_2\text{---}S(O)CH_3)CONH\text{---}CH(Phe)\text{---}CH_2\text{---}COOCH_2Phe$ The final compound of Example 27, protected on the amine function, is oxidized under the conditions described in Example 4. After deprotection with TFA (Example 1, step 3), the expected compound is obtained. Overall Yld 53%. Rf (8:2 $CH_2Cl_2$/MeOH)=0.35.

EXAMPLE 29

Preparation of
$H_2N\text{---}CH(CH_2CH_2SCH_3)CH_2\text{---}S\text{---}S\text{---}CH_2\text{---}CH(CH_2CH_2\text{---}SCH_3)\text{---}CONH\text{---}CH(CH_2Phe)\text{---}CH_2\text{---}COOCH_2Phe$ 0.83 g of the disulfide (Example 5, step 1) is condensed under the conditions of Example 1, step 2, with 1.07 g of benzyl 3-[N-(2-mercaptomethyl-4-methylmercapto-1-oxobutyl)amino]- 4-phenylbutanoate. 1.22 g (72%) of the final compound protected on the amine function are obtained. Rf (7:3:0.5 cyclohexane/EtOAc/AcOH)=0.41. Treatment with TFA (Example 1, step 3) liberates the final compound (0.79 g) (Yld 72%) Rf (7:3 $CH_2Cl_2$/MeOH): 0.70.

EXAMPLE 30

Preparation of
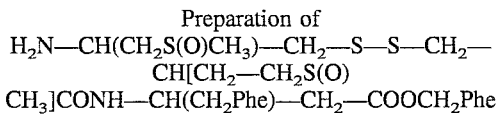

The final compound of Example 29, protected on the amine function, is oxidized under the conditions of Example 8. After deprotection with TFA (Example 1, step 3), the expected compound is obtained. Overall Yld 68%. Rf (8:2 $CH_2Cl_2$/MeOH)=0.33.

EXAMPLE 31

Preparation of

0.95 g of the disulfide (Example 5, step 1) is condensed under the conditions of Example 1, step 2, with 1.13 g of benzyl 2-[N-(2-mercaptomethyl-4-methylmercapto-1-oxobutyl)amino]cyclohexanecarboxylate. 1.43 g (78%) of the final product protected on the amine function are obtained. Rf (7:3:0.5 cyclohexane/EtOAc/AcOH)=0.39. Treatment with TFA (Example 1, step 3 ) liberates the final compound (0.88 g) (Yld 75%) Rf (7:3 $CH_2Cl_2$/MeOH): 0.65.

EXAMPLE 32

Preparation of

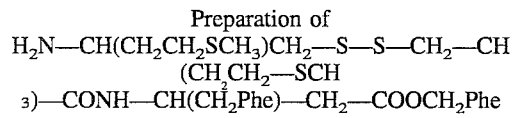

The compound protected on the amine function of Example 31 is oxidized under the conditions of Example 8. After deprotection with TFA (Example 1, step 3), the expected compound is obtained. Overall Yld 58%. Rf (8:2 $CH_2Cl_2$/MeOH)=0.30.

EXAMPLE 33

Preparation of $H_2N-CH(CH_2CH_2S(O)CH_3)CH_2-S-S-CH_2-CH(CH_2CH(CH_3)_2)CONH-N$ 

The compound protected on the amine function of Example 5, step 1, is condensed with N-morpholinyl (isopropylmethyl)-3-mercaptopropanamide under the conditions of Example 5, step 2. The compound obtained is then oxidized with sodium periodate and is thereafter deprotected with trifluoroacetic acid under the conditions of Example 8 to yield the final compound. Overall yield: 62%. Rf (8:2 $CH_2Cl_2$/MeOH)= 0.12.

EXAMPLE 34

Biological activity of the compounds according to the invention

The biological activity relates to the inhibition of purified aminopeptidase N and of purified neutral endopeptidase.

1) In vitro inhibition of enkephalinase activities.

a) Inhibitory potency against neutral endopeptidase

The inhibitory power is determined on purified rabbit kidney neutral endopeptidase following the protocol described in the literature (Blumberg et al. Life Sci. (1981) 28, 301). After a preincubation for 15 minutes at 25° C., an aliquot of proteins is incubated for 20 minutes at 25° C. in the presence of 20 nmol of ($^3$H)-D-Ala$^2$-Leu$^5$-enkephalin and the test compound in solution in Tris-HCl buffer (pH 7.4) in the presence of dithiothreitol DTT (100 equivalents relative to the inhibitor). The reaction is stopped by adding 0.2 N HCl. The tritiated metabolite ($^3$H)-Tyr-D-Ala-Gly is separated from the D-Ala$^2$-Leu$^5$-enkephalin by chromatography on a Porapak column, and the quantity formed measured using a liquid scintillation counter.

b) Inhibitory potency against aminopeptidase N

The inhibitory power is measured on purified porcine kidney aminopeptidase (Boehringer, France). The assay is performed in a manner identical to the above, using ($^3$H)-Leu$^5$-enkephalin as a substrate. The metabolite formed, ($^3$H)-Tyr, is separated by chromatography on a Porapak column, and the quantity formed measured using a liquid scintillation counter.

The activity of the different compounds is expressed as 50% inhibitory concentrations (IC$_{50}$), and the results are summarized in Table II.

TABLE II

| | IC$_{50}$ Neutral endopeptidase | IC$_{50}$ Aminopeptidase N |
|---|---|---|
| Final compound of Example 1 | 2*10$^{-9}$M | 5*10$^{-9}$M |
| Final compound of Example 2 | 2.5*10$^{-9}$M | 5*10$^{-9}$M |
| Final compound of Example 3 | 1.2*10$^{-9}$M | 5*10$^{-9}$M |
| Final compound of Example 4 | 2*10$^{-9}$M | 8*10$^{-9}$M |
| Final compound of Example 5 | 2*10$^{-9}$M | 2*10$^{-9}$M |
| Final compound of Example 6 | 1.2*10$^{-9}$M | 2*10$^{-9}$M |
| Final compound of Example 7 | 2.5*10$^{-9}$M | 2*10$^{-9}$M |
| Final compound of Example 8 | 2*10$^{-9}$M | 2*10$^{-9}$M |

TABLE II-continued

| | IC$_{50}$ Neutral endopeptidase | IC$_{50}$ Aminopeptidase N |
|---|---|---|
| Final compound of Example 22 | 7*10$^{-9}$M | 2*10$^{-9}$M |
| Final compound of Example 26 | 5*10$^{-9}$M | 2*10$^{-9}$M |
| Final compound of Example 28 | 3*10$^{-9}$M | 2*10$^{-9}$M |
| Final compound of Example 30 | 3*10$^{-9}$M | 2*10$^{-9}$M |
| Final compound of Example 32 | 4*10$^{-9}$M | 2*10$^{-9}$M |
| Final compound of Example 33 | 5*10$^{-9}$M | 2*10$^{-9}$M |

Identical inhibitory powers are obtained against these two enzymes after incubation of the compounds with rat brain membrane fractions in place of dithiothreitol.

2) "In vivo" inhibition of cerebral NEP

The enzymatic activity of cerebral NEP is compared in mice untreated or treated with a given dose of compound (approximately 2.5 mg/kg injected intravenously. The animals are sacrificed at variable times after injection of the inhibitor, and the NEP activity is determined in the brain by measuring the degradation of ($^3$H)-D-Ala$^2$-Leu$^5$-enkephalin.

For the final compound of Example 1, injected at a dose of 2.7 µmol/kg (47.6 µg in 100 µl), the following results are obtained:

| time | % inhibition cerebral NEP |
|---|---|
| 15' (n = 4) | 96 ± 9 |
| 60' (n = 4) | 68 ± 4 |
| 120' (n = 4) | 63 ± 2 |
| 180' (n = 4) | 42 ± 16 |

For the final compound of Example 7, the following are obtained under the same conditions:

| time | % inhibition cerebral NEP |
|---|---|
| 60' (n = 4) | 96 ± 5 |
| 120' (n = 5) | 96 ± 4 |
| 180' (n = 5) | 92 ± 4 |

EXAMPLE 35

Pharmacological study of the compounds a) Acute toxicity

Determination of the mortality in mice is observed following a single intravenous administration of increasing doses of the test compounds. The LD$_{50}$ for all the compounds studied is greater than 100 mg/kg i.v.

b) Antalgic activity

1) Hot plate test: This involves the licking and jumping reflex of the mouse on a plate heated to 55° C., according to the method of Jacob et al (Arch Int. Pharmacodyn. 122 287, 1959; 1961).

1.1. Administered i.v. (100 μl in tail vein) in mice, the compounds tested display a characteristic effect both on the latency time of jumping and on latency time of licking. These effects are antagonized by naloxone (0.5 mg/kg s.c.).

The results are expressed in Table III as a % analgesia. The percentage analgesia is expressed for each dose of compound tested by the following formula:

$$\% \text{ analgesia} = \frac{\left(\begin{array}{c}\text{measured latency} \\ \text{time}\end{array} - \begin{array}{c}\text{control latency} \\ \text{time}\end{array}\right)}{\left(\begin{array}{c}\text{maximum latency} \\ \text{time}\end{array} - \begin{array}{c}\text{control latency} \\ \text{time}\end{array}\right)},$$

TABLE III

| Compound | 50% analgesia | 50% analgesia |
| --- | --- | --- |
| Final compound of Example 1 | 4 mg/kg | 20 mg/kg |
| Final compound of Example 5 | 2.5 mg/kg | 10 mg/kg |
| Final compound of Example 7 | 5 mg/kg | 15 mg/kg |
| Final compound of Example 8 | 2.5 mg/kg | 10 mg/kg |
| Final compound of Example 22 | 4.5 mg/kg | 25 mg/kg |
| Final compound of Example 26 | 8 mg/kg | 30 mg/kg |
| Final compound of Example 28 | 4 mg/kg | 15 mg/kg |
| Final compound of Example 30 | 3 mg/kg | 15 mg/kg |
| Final compound of Example 32 | 2 mg/kg | 10 mg/kg |

1.2 Administered i.p. in mice, the test compounds display a characteristic effect on the times of restraint of jumping and of licking. These effects are antagonized by naloxone (0.5 mg/kg).

| | |
| --- | --- |
| Compound of Example 1 | 10 mg/kg |
| Compound of Example 5 | 7 mg/kg |
| Compound of Example 7 | 8 mg/kg |
| Compound of Example 22 | 6 mg/kg |
| Compound of Example 32 | 5.5 mg/kg |

2) Test on abdominal cramps (Hendershot and Forsaith. J. Pharmacol. (1975), 125, 237): This test measures the number of cramps induced by i.p. injection of 100 μl of a 0.02% solution of phenylbenzoquinone. The number of cramps is counted during 10 minutes, 10 minutes after the injection. Administered i.v., the compounds decrease the number of cramps.

| | dose | % analgesia |
| --- | --- | --- |
| Final compound of Example 1 | 1 mg/kg | 24.6% ± 8 |
| Final compound of Example 1 | 3 mg/kg | 46.9% ± 7.9 |
| Final compound of Example 1 | 9 mg/kg | 73.9% ± 8.2 |
| Final compound of Example 7 | 2.5 mg/kg | 32% ± 4 |
| Final compound of Example 7 | 5 mg/kg | 68% ± 9 |
| Final compound of Example 7 | 10 mg/kg | 95% ± 4 |

3) Test of withdrawal of the tail in rats: (tail flick test): administered i.v. in rats, the compounds according to the invention produce a significant extension of the time of withdrawal of the tail. These effects are antagonized by naloxone (0.5 mg/kg s.c.).

The results are expressed as a % analgesia for the same dose (10 mg/kg) of all the compounds tested.

| | % analgesia |
| --- | --- |
| Compound of Example 1 | 20% |
| Compound of Example 5 | 25% |
| Compound of Example 7 | 42% |
| Compound of Example 32 | 36% | c) Potentiation of the behavioral effects (locomotor hyperactivity) induced by the compounds according to the invention after long-term treatment with antidepressants:

1 h after i.v. or p.o. administration in rats, the compounds according to the invention induce an increase in locomotor activity. This effect is considerably increased after long-term treatment with neuroleptics such as sulpiride (100 mg/kg i.p. every day). This potentiation is not apparent until three weeks after the beginning of the treatment with neuroleptics. The results show an increase in the concentration of endogenous enkephalins, in agreement with the results obtained with morphine by Stinus et al. (psychoparmacology, 85, 323, (1985).

| Results* | Locomotor activity** |
| --- | --- |
| control rat*** | 100% |
| rat treated i.v. with the compound of Example 5 (5 mg/kg) | 400% |
| rat treated i.v. with the compound of Example 7 (3 mg/kg) | 400% |
| rat treated i.v. with the compound of Example 30 (2 mg/kg) | 350% |
| rat treated i.v. with the compound of Example 30 (20 mg/kg) | 370% |

*after three weeks of long-term treatment with sulpiride
**measured by the number of righting movements
***corresponds to animals given long-term treatment with sulpiride but which did not receive an inhibitor.

d) Mice despair test

This test, described by Porsolt et al. (Arch. Int. Pharmacodyn. Ther, 299, 327 (1977), enables the antidepressant properties of the claimed compounds to be evaluated.

Mice are treated with increasing doses of the compounds thirty minutes before the test, and the immobility of the animals is measured relative to controls which receive only the vehicle. The immobility time is decreased by the compounds according to the invention, and this effect is antagonized by naloxame (0.5 mg/kg s.c.).

| Results | Immobility time (s) |
| --- | --- |
| controls | 165 ± 15 |
| mouse treated with compound Ex. 5 (5 mg/kg i.p.) | 108 ± 12* |
| mouse treated with compound Ex. 30 | |
| (2 mg/kg i.p.) | 96 ± 8* |
| (20 mg/kg p.o.) | 101 ± 10* |

*$p < 0.01$.

e) Study of the tolerance and addiction effects induced by long-term administration of the compound of Example 8:

1) The compound 8 is administered s.c. four times per 24 hours at a dose of 5 mg/kg for 6 days to mice and at 10 mg/kg to rats.

Morphine (hydrochloride) is administered under the same conditions (0.5 mg/kg in mice, 2 mg/kg in rats). The control animals receive only the vehicle.

| Results in % analgesia relative to the controls | | | |
|---|---|---|---|
| | days | | |
| | 0 | 1 | 6 |
| mouse/morphine | 100 ± 10 | 60 ± 10 | 0 |
| rat/morphine | 70 ± 12 | 20 ± 3 | 0 |
| mouse/compound 8 | 100 ± 10 | 100 ± 8 | 70 ± 15 |
| rat/compound 8 | 40 ± 5 | 40 ± 5 | 30 ± 7 |
| rat/compound 7 | 100 ± 10 | 100 ± 8 | 80 ± 10 |

2) After long-term treatment for 6 days under the conditions described above, the rats undergo an injection of 2 mg/kg of naloxane s.c. The signs of abstinence syndrome are measured according to Cowan et al. (J. Pharmacol. Exp. Ther. (1988) 246, 950).

Compared to morphine, long-term treatment with the compound 8 gives rise to very weak addiction effects, illustrated by the absence of jumps, absence of fall in temperature and absence of hair loss which are the most severe signs of a habituation crisis.

3) Injection i.v. of the compound 7 into an animal (mouse or rat) which is morphine-tolerant leads to an analgesic response identical to that obtained in a control animal. This demonstrates the absence of cross-tolerance between morphine and the compound 7.

The subject of the invention is, moreover, methods for the treatment of depression and pain, in which effective quantities of at least one of the compounds described above are administered to the individual to be treated. The administration routes suited to said methods are those common in these types of treatment, especially the intravenous, oral, subcutaneons or intraperitoneal route.

We claim:

1. A compound of the formula $$H_2N-CH(R_1)-CH(R_2)-S-S-CH(R_3)-CH(R_4)-A-B-Z$$

in which $R_1$ is saturated or unsaturated, linear or branched hydrocarbon chain containing from 1 to 6 carbon atoms, unsubstituted or substituted with =OR in which R is hydrogen, a linear or branched C1 to C4 hydrocarbon chain or phenyl or benzyl; =SR, R having the same definition as above, or an oxidized thioether group S(O)R, R having the same definition as above, methylcycloalkyl of 5 to 6 carbon atoms, benzyl or phenyl optionally substituted:
  with 1 to 5 halogen,
  or OR' or SR', R' being an alkyl group having 1 to 4 carbon atoms, =SR' being optionally oxidized on the sulfur atom, or with an amino group optionally mono- or disubstituted with an aliphatic of 1 to 6 carbon atoms, optionally oxidized on the amine, $R_2$ is hydrogen or methyl, $R_3$ is hydrogen or a linear or branched alkyl chain, $R_4$ is saturated or unsaturated, linear or branched hydrocarbon chain containing from 1 to 6 carbon atoms, unsubstituted or substituted with a hydroxyl group, =OR in which R has the same meaning as above, =SH, =SR thioether group oxidized to sulfoxide, or a methylcycloalkyl group having 5 to 6 carbon atoms, a benzyl or phenyl group, optionally substituted with 1 to 5 halogen, with a hydroxyl or a thiol, =OR' or =SR', R' being alkyl of 1 to 4 carbon atoms, the thioether being optionally oxidized on the sulfur atom, with an amino group optionally mono- or disubstituted with an aliphatic of 1 to 6 carbon atoms, optionally oxidized on the amine function, Z is $-CH(R_5)-CH(R_6)_n-COO(R_7)$ in which $R_5$ and $R_6$ are individually selected from the group consisting of hydrogen,
  alkyl group having 1 to 6 carbon atoms, unsubstituted or substituted with hydroxyl or =OR, =SH or =SR groups,
  or a phenyl (Phe) or benzyl unsubstituted or substituted with 1 to 5 halogen atoms; =OR' or =SR', R' having the definition specified above, $R_5$ and $R_6$ can also each represent saturated or unsaturated hydrocarbon chains containing from 1 to 6 carbon atoms in which 1 to 2 carbon atoms may be substituted by an oxygen, sulfur or nitrogen atom, capable of leading to the formation of one or more saturated or aromatic 5- to 6-membered hydrocarbon rings, n is 0 or 1, $R_7$ is selected from the group consisting of hydrogen, saturated or unsaturated, linear or branched alkyl group having 1 to 6 carbon atoms and benzyl, A—B represents an amide CONH or retro-amide NHCO in the forms of racemic mixtures or in the form of enantiomers, of diastereoisomers or of stereoisomers, as well as mixtures thereof and their non-toxic, pharmaceutically acceptable salts.

2. Compounds according to claim 1 characterized in that Z is $$-CH(R_5)-(CH(R_6))_n-COO(R_7)$$

$R_2$ and $R_3$ both are hydrogen, AB is an amide link COHN, $R_1$ is $-CH_2CH_2S(O)CH_3$ and $R_7$ is benzyl.

3. Compounds according to claim 2, characterized in that $R_4$ represents $-CH_2-CH_2S(O)CH_3$.

4. Compound according to claim 2, corresponding to the formula:

$$H_2N-CH(CH_2CH_2S(O)CH_3)-CH_2S-S-CH_2-CH(CH_2Phe)CONHCH_2 \ COOCH_2Phe$$

5. Compound according to claim 2, corresponding to the formula:

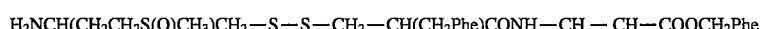
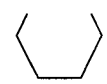

6. Compound according to claim 3, corresponding to the formula:

$$H_2N-CH(CH_2CH_2S(O)CH_3)CH_2-S-S-CH_2CH(CH_2CH_2S(O)CH_3)CONHCH(CH_3)-COOCH_2Phe.$$

7. Compound according to claim 3, corresponding to the formula:

H₂N—CH(CH₂CH₂S(O)CH₃)—CH₂—S—S—CH₂—CH(CH₂CH₂S(O)CH₃)CONHCH (Phe)—CH₂—COOCH₂Phe.

8. Compound according to claim 3, corresponding to the formula:

H₂N—CH(CH₂CH₂S(O)CH₃)—CH₂—S—S—CH₂—CH(CH₂CH₂S(O)CH₃)CONHCH (CH₂Phe)—CH₂COOCH₂Phe.

9. Compound according to claim 3, corresponding to the formula:

H₂N—CH(CH₂CH₂S(O)CH₃)CH₂—S—S—CH₂—CH(CH₂CH₂S(O)CH₃)CONH—CH—CH—COOCH₂Phe.

10. Compound according to claim 1, corresponding to the formula:

H₂NCH(CH₂CH₂SCH₃)CH₂S—S—CH₂CH(CH₂CH(CH₃)₂)CONHCH(CH₃) COOCH₂Phe.

11. Compound according to claim 1, corresponding to the formula:

H₂NCH(CH₂CH₂SCH₃)CH₂—S—S—CH₂—CH(CH₂CH₂SCH₃)CONHCH(CH₃) COOCH₂Phe.

12. Compound according to claim 1, corresponding to the formula:

H₂N—CH(CH₂CH(CH₃)₂)—CH₂—S—S—CH₂—CH(CH₂Phe)CONH—CH₂ COOCH₂Phe.

13. Compound according to claim 1, corresponding to the formula:

H₂N—CH(CH₂CH(CH₃)₂)—CH₂—S—S—CH₂—CH(CH₂Phe)CONH—CH(CH₃) COOCH₂Phe.

14. Compound according to claim 1, corresponding to the formula:

H₂N—CH(CH₂CH(CH₃)₂)—CH₂—S—S—CH₂—CH(CH₂Phe)CONH—CH(CH₂Phe)—COOCH₂Phe.

15. Compound according to claim 1, corresponding to the formula:

H₂N—CH(CH₂CH₂SCH₃)—CH₂—S—S—CH₂—CH(CH₂Phe)CONH—CH₂—COOCH₂Phe.

16. Compound according to claim 1, corresponding to the formula:

H₂N—CH(CH₂CH₂SCH₃)—CH₂—S—S—CH₂—CH(CH₂Phe)CONH—CH(CH₃) COOCH₂Phe.

17. Compound according to claim 1, corresponding to the formula:

H₂N—CH(CH₂CH₂SCH₃)CH₂—S—S—CH₂—CH(CH₂Phe)CONH—CH(CH₂Phe) COOCH₂Phe.

18. Compound according to claim 1, corresponding to the formula:

H₂N—CH(CH₂CH₂S(O)CH₃)—CH₂—S—S—CH₂—CH(CH₂Phe)—CONH—CH (CH₂Phe)—COOCH₂Phe.

19. A method of relieving pain in warm-blooded animals comprising administering to warm-blooded animals an analgesically effective amount of a compound of claim 1.

20. An analgesic composition comprising an analgesically effective amount of a compound of claim 1 and an inert pharmaceutical carrier.

* * * * *